US008696605B2

(12) United States Patent
Nichols

(10) Patent No.: US 8,696,605 B2
(45) Date of Patent: Apr. 15, 2014

(54) PERSONAL CARE VAPORIZER DEVICE FOR HANDS

(76) Inventor: Thomas Nichols, Laguna Niguel, CA (US)

(*) Notice: Subject to any disclaimer, the term of this patent is extended or adjusted under 35 U.S.C. 154(b) by 218 days.

(21) Appl. No.: 13/413,491

(22) Filed: Mar. 6, 2012

(65) Prior Publication Data

US 2012/0222696 A1    Sep. 6, 2012

Related U.S. Application Data

(63) Continuation-in-part of application No. 12/079,747, filed on Mar. 27, 2008, now Pat. No. 8,157,753.

(51) Int. Cl.
*A61H 1/00* (2006.01)

(52) U.S. Cl.
USPC ............................................................ 601/17

(58) Field of Classification Search
USPC .................. 601/2, 15–18, 46, 64, 154, 160; 604/289–291, 310; 261/18, 18.1; 15/110; 607/84, 104
See application file for complete search history.

(56) References Cited

U.S. PATENT DOCUMENTS

| 2,074,838 | A | 3/1937 | Geria et al. ........................ 4/165 |
| 2,265,484 | A | 12/1941 | Hillebrand ........................ 4/165 |
| 3,918,987 | A | 11/1975 | Kopfer ............................ 134/95 |
| 4,331,137 | A | 5/1982 | Sarui ........................ 128/200.16 |
| 4,616,122 | A | 10/1986 | Burian ............................ 219/273 |
| 4,670,010 | A * | 6/1987 | Dragone ........................ 604/289 |
| 5,074,322 | A * | 12/1991 | Jaw ............................. 134/56 R |
| 5,098,414 | A | 3/1992 | Walker ............................ 604/291 |
| D342,992 | S | 1/1994 | Robertson ..................... D23/270 |
| 6,090,085 | A | 7/2000 | Mehl, Sr. ....................... 604/291 |
| 6,343,425 | B1 | 2/2002 | Sias et al. ........................ 34/389 |
| 6,573,420 | B2 | 6/2003 | Stapf et al. ...................... 602/42 |
| 6,706,243 | B1 | 3/2004 | Sias et al. ........................ 422/28 |
| 6,755,398 | B1 * | 6/2004 | Wong .............................. 261/81 |
| 6,805,678 | B2 * | 10/2004 | Cafaro ............................ 601/16 |
| 7,934,703 | B2 * | 5/2011 | Tomono et al. .............. 261/18.1 |
| 2004/0084787 | A1 * | 5/2004 | Williams et al. ............. 261/72.1 |
| 2004/0158919 | A1 | 8/2004 | Fung ................................ 4/537 |
| 2006/0208104 | A1 | 9/2006 | DeBoer ........................ 239/318 |
| 2007/0123808 | A1 | 5/2007 | Rhoades ......................... 601/73 |

* cited by examiner

*Primary Examiner* — Patricia Bianco
*Assistant Examiner* — Raymond E Harris
(74) *Attorney, Agent, or Firm* — Steins & Associates, P.C.

(57) ABSTRACT

The main housing is defined by a large aperture formed in its side. The side aperture provides access to an internal treatment chamber. The user can insert one or both hands into the chamber through the side aperture to provide therapeutic treatment for the skin of the hands. The device has a removable fluid reservoir seatable into the main housing. Fluid from the reservoir is ported to an internal cool mist vaporizor such as a transducer or other misting apparatus. The mist is driven down a mist conduit by user-adjustable airflow. As the mist passes down the mist conduit, it passes a heating element that allows the user to selectively deliver heated or cool vapor into the treatment chamber. The user may utilize water and/or fluid having additives such as extracts, therapeutic medications and essential oils as the raw material for mist formation.

19 Claims, 6 Drawing Sheets

PERSONAL CARE VAPORIZER DEVICE FOR HANDS

This application is a continuation-in-part of application Ser. No. 12/079,747, filed Mar. 27, 2008 ("the parent application") now U.S. Pat. No. 8,157,753.

BACKGROUND OF THE INVENTION

1. Field of the Invention

This invention relates generally to skin care devices and methods and, more specifically, to a Personal Care Vaporizer Device for Hands.

2. Description of Related Art

Skin treatment devices are plentiful. Some pertinent examples of conventional devices and systems in this field are: Mehl, Sr., et al., U.S. Pat. No. 6,090,085, Walker, U.S. Pat. No. 5,098,414, and Burian, U.S. Pat. No. 4,616,122.

Mehl is a "Skin Moisturizing and Buffing Device." The Mehl system combines a handheld facial buffer that has an internal steam generator for creating a stream of steam for emission through the "movable skin contacting assembly" (i.e. the facial buffer head). While the Mehl device does provide a handheld steam buffer, it fails to allow the user the option of either cool vapor or heated steam emitted through the buffer head. Furthermore, the amount of vapor available for use is severely limited due to the entire package being of handheld size. A device providing a large volume liquid reservoir that can emit either heated steam or cool vapor would provide a wider set of benefits to the user.

Walker is a "Steam Device for Cosmetic Skin Treatment." The Walker device does provide a large water reservoir for use in steam emission, but it fails to provide the option of cool vapor.

The Burian "Electrically Heated Facial Sauna Vapor Generating Apparatus," like Walker discloses a large-reservoir, steam generating facial massage device. Just as with Walker, Burian fails to suggest the generation of cool vapor (in addition to hot steam) for facial application through the massage head. The ability to deliver hot or cool vapor through the massage head allows the user to continue the facial massage while heating and cooling the massage head and skin. If only the only option is to deliver steam, then the user must either stop the massage or stop the vapor delivery in the event that the face becomes uncomfortably hot.

In the field of hand skin treatment devices and system, the following references are relevant: Dragone, U.S. Pat. No. 4,670,010, Jaw, U.S. Pat. No. 5,074,322, Robertson, U.S. Pat. No. D342,992, M. Geria, U.S. Pat. No. 2,074,838 and Kopfer, U.S. Pat. No. 3,918,987. Each of these prior devices relates to the cleansing of a person's hands, rather than to the application of liquid vapor for the purpose of improving the skin condition of the person's hands.

Dragone is a "Liquid-nebulizing Device for the Dermatological Treatment of the Hands" that has a spray atomizer for dispensing disinfecting liquid onto the user's hands. There is not option of applying cool or warm vapor for the purpose of improving the quality of the skin.

Jaw discloses the "Structure of Sterilizing Hand Dryer" that permits the user to insert his or her hands into the cleaning chamber, wherein sterilizing liquid is first sprayed on the hands, and then warm, air is applied to dry the hands. There is no suggestion of therapeutic application of cool or warm vapor/mist to the hands.

Robertson as a design patent, simply discloses a boxy, single aperture, "sanitizing station for limbs." From the disclosure, it is uncertain what functionality is offered to the user, beyond that the user apparently inserts his or her hands into the front opening for "sanitizing."

M. Geria is a "Heating Device for Limb Extremities" that does enable the user to apply heated air to the limbs. However, there is no potential for the application of fluid mist onto the limbs, whether warm or cool mist/vapor.

Finally, Kopfer is a "Surgeon Hand and Arm Scrubbing Apparatus" that has a pair of cavities formed within the main housing. The user inserts his or her hands into the cavities and internal nozzles eject streams of fluid into the cavities. The Kopfer device is quite elaborate in its design, but is limited to cool water spray or warm air with sterilizing vapor. There is no capability to manually select cool or warm liquid vapor for application to one's hands.

SUMMARY OF THE INVENTION

In light of the aforementioned problems associated with the prior devices and methods, it is an object of the present invention to provide a Personal Care Vaporizer Device for Hands. The device should have a main housing that is defined by a large aperture formed in its side. The side aperture should provide access to an internal treatment chamber. The user should be able to insert one or both hands into the chamber through the side aperture in order to provide therapeutic treatment for the skin of the hands. The device should have a removable fluid reservoir that seats into the main housing. Fluid from the reservoir should be ported to an internal cool mist vaporizor such as a transducer or other misting apparatus. Once vaporized, the mist should be driven down a mist conduit by user-adjustable airflow. As the mist passes down the mist conduit, it should pass a heating element that allows the user to selectively deliver heated or cool vapor into the treatment chamber. The user should be able to utilize water and/or fluid having additives such as extracts, additives, therapeutic medications and essential oils as the raw material for formation of the mist.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invent ion have been defined herein specifically to provide a Personal Care Vaporizer Device for Hands.

Figure 1:
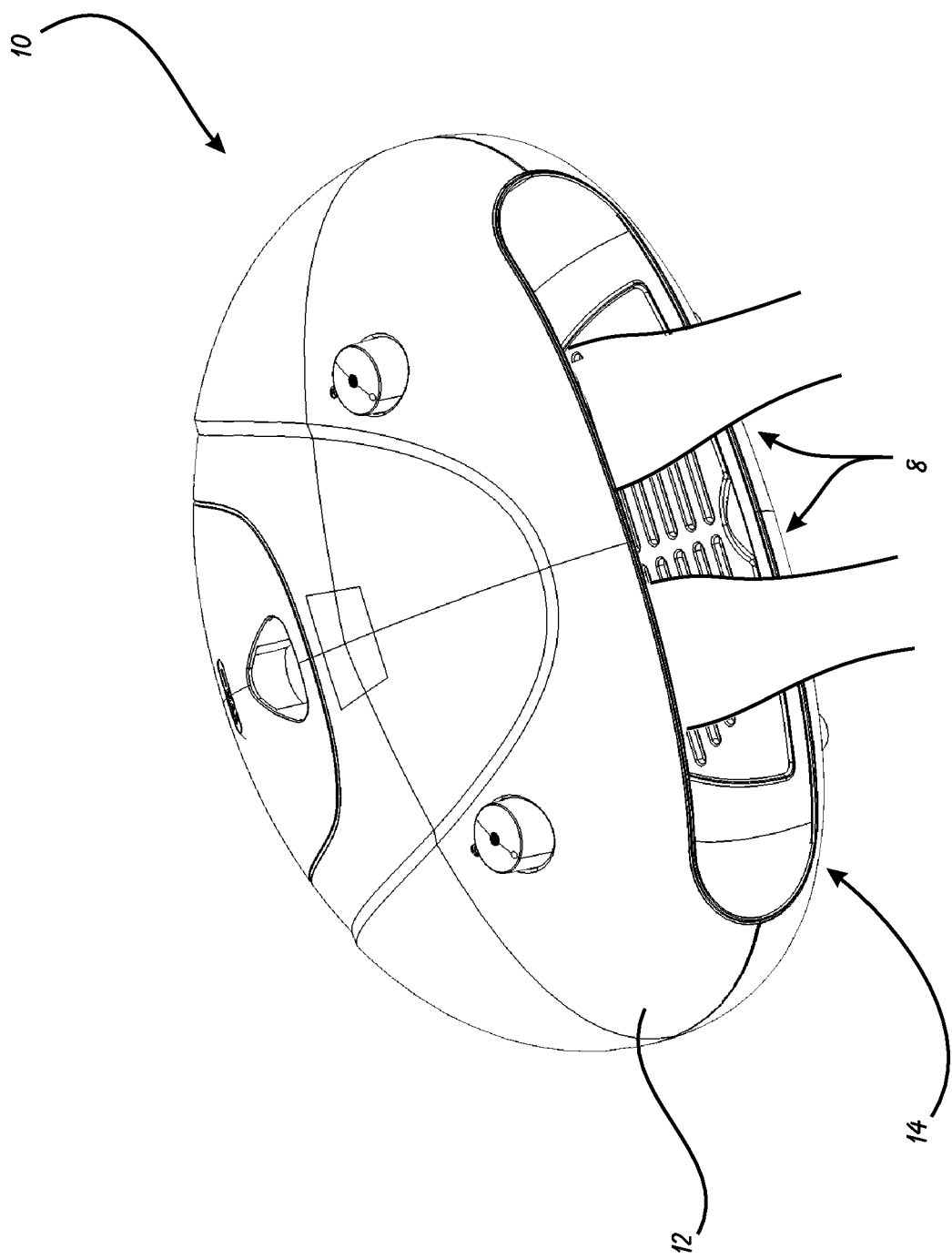
FIG. 1 is a front perspective view of a preferred embodiment of the personal care vaporizor device for hands of the present invention.
Figure 2:
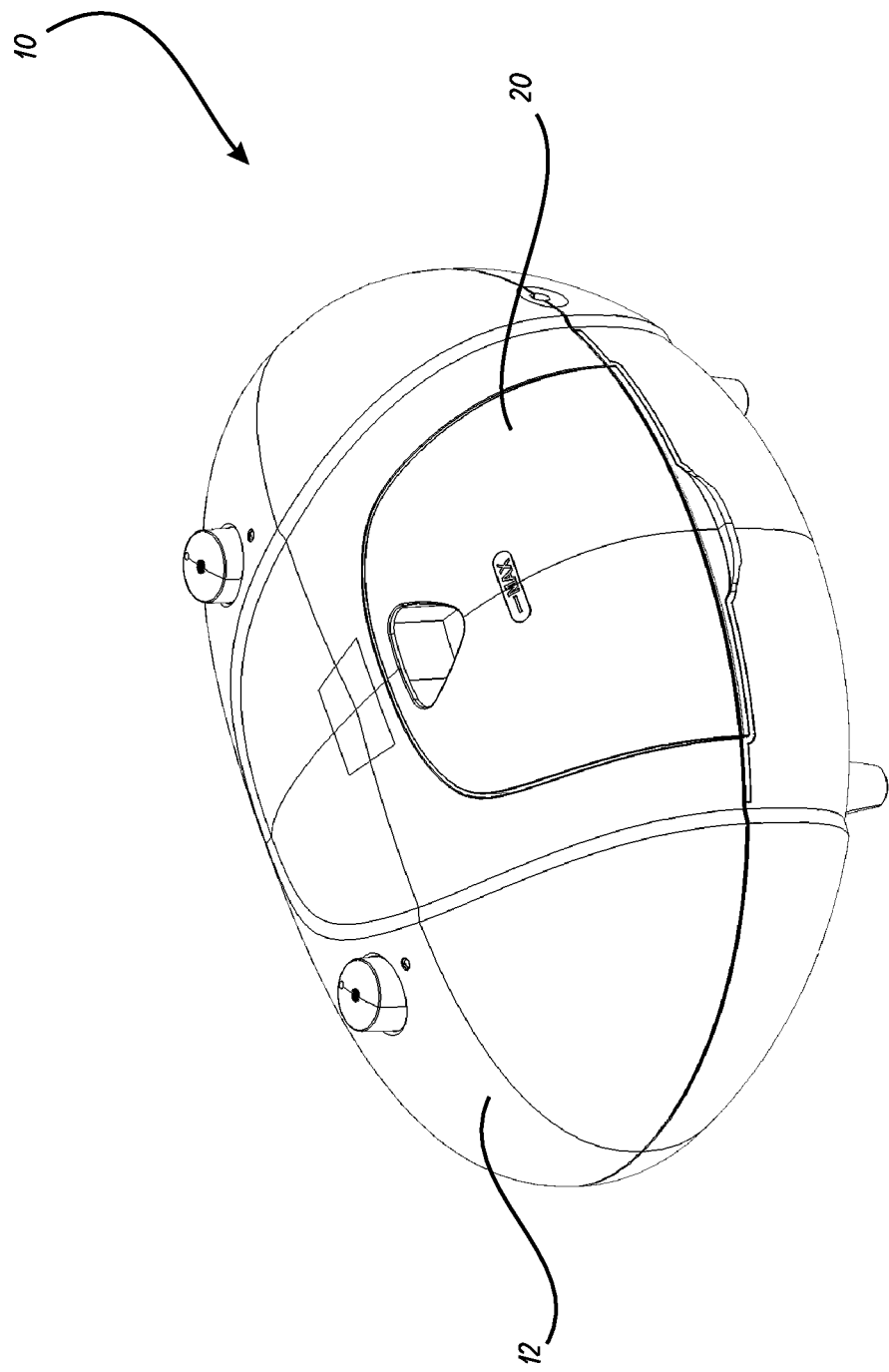
FIG. 2 is a rear perspective view of the device of FIG. 1.

The present invention can best be understood by initial consideration of FIGS. 1 and 2 FIG. 1 is a front perspective view of a preferred embodiment of the personal care vaporizor device for hands 8 of the present invention. While the device of the parent application incorporated a separate base unit and handheld applicator, the present device 10 is a single-housing unit, in order to free up the user's hands so as to permit users to treat their own hands without third party assistance. Similar to the device of the parent application, the device 10 of the present invention generates cool vapor from liquid contained in an internal liquid reservoir. The cool vapor, once created, can either be administered to the user's skin, or it can first be heated within the device 10 prior to application.

In order to utilize the device 10, the user inserts his or her hands 8 into the treatment chamber 14 formed in the main housing 12. FIG. 2 is a rear perspective view of the device 10 of FIG. 1. The back side of the main housing 12 has a removeable fluid reservoir 20, that is shown as it would be (in place in the housing 12) during operation. The operational modes of the device 10 are described below in connection with FIG. 3.

Figure 3:
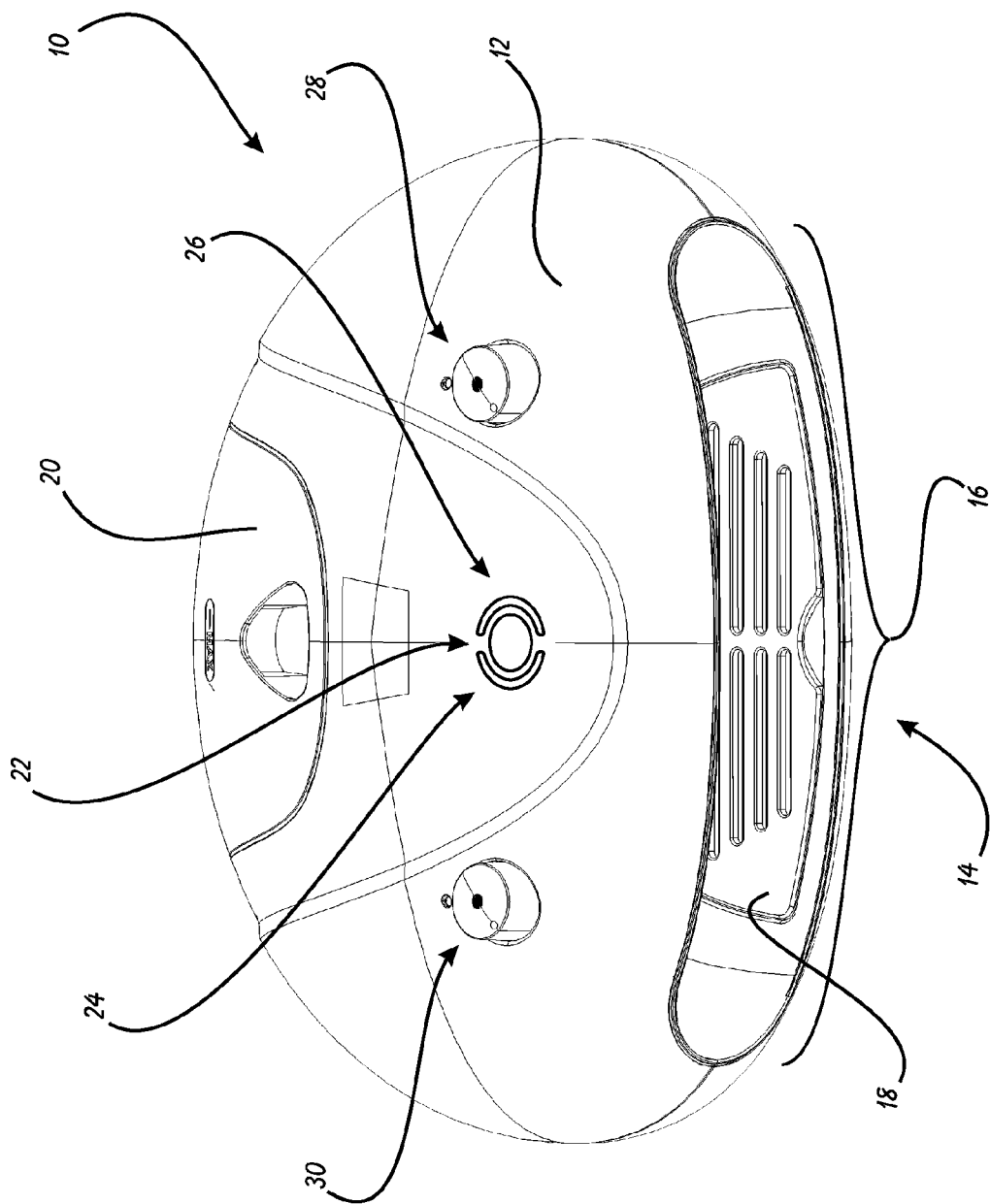
FIG. 3 is a top perspective view of the device of FIGS. 1 and 2.

FIG. 3 is a top perspective view of the device 10 of FIGS. 1 and 2. The main housing 12 is generally ovoid or rounded in shape, and is defined by the removeable fluid reservoir 20 at its rear side. An aperture 16 is formed on the front side of the main housing 12, opposite the fluid reservoir 20. The aperture 16 is sized tall and wide enough in order to comfortably accept a pair of adult human's hands therethrough.

The internal treatment chamber 14 is accessed through the aperture 16 by the user inserting his or her hands therethrough (as depicted above in FIG. 1). A drip tray 18 is located in the bottom of the treatment chamber in order to separate the runoff and/or residue from the condensed vapor from the inside of the treatment chamber 14 (and the user's hands). There are a number of operational modes related to the generation and application of treatment vapor to the user's hands. The mode control button 22 is a touch-sensitive, preferably waterproof (or water resistant) switch that the user activates to selectively operate the different modes of the device 10. There are 2 basic modes available: (1) cool mist and (2) heated mist. Depression of the mode control button 22 will cycle between cool mist, heated mist and off.

Bracketing, or otherwise in close proximity to, the mode control button 22 are a water/mist status indicator lamp 24. The water/mist status indicator lamp 24 provides a visual display when either cool or heated vapor/mist is being emitted (lamp illuminated). The lamp 24 also will provide indication when the fluid level in the reservoir 20 is low.

The heating element status indicator 26 illuminates when the heating element is turned on while at the same time as mist/vapor is being generated. If the heater is active when the mist/vapor generator is deactivated (by the mode control button 22), then the heater will also deactivate and both status indicators 24, 26 will be extinguished in their preferred form.

Two additional control elements are located on opposing ends of the top surface of the main housing 12 of the device 10. A mist control knob 30 is used to control the amount of mist generated by the internal vapor generator. An airflow control knob 28 is used to control the volume (and speed) of airflow driving the generated mist into the treatment chamber 14. While airflow can be generated without mist, the opposite is not the case—in order to generate mist, there must be airflow in order to drive the generated mist/vapor through the internal plumbing of the device 10 and onto the user's hands. Now turning to FIGS. 4 and 5, we can examine the internal components of this novel device 10.

Figure 4:
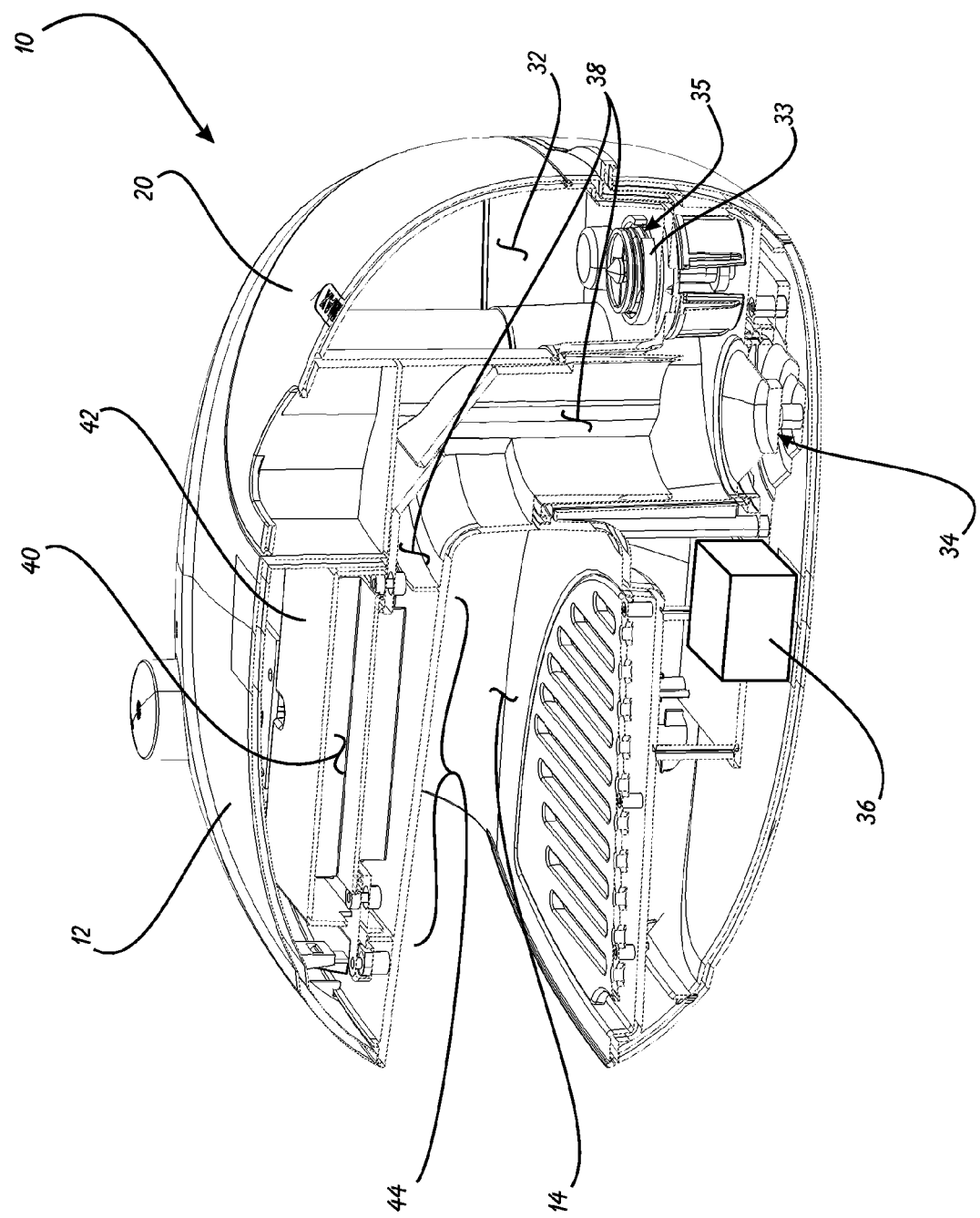
FIG. 4 is a partially cutaway side view of the device of FIGS. 1-3.

FIG. 4 is a partially cutaway side view of the device 10 of FIGS. 1-3. The removable fluid reservoir 20 is a (preferably plastic) housing containing, among other elements, a fluid chamber 32. The fluid chamber 32 is a water-tight reservoir within which fluid is placed and stored for use by the device 10. In order to re-fill the fluid chamber 32, the fluid reservoir 20 is removed from its alcove formed in the main housing 12 and turned over. Water and other fluids or treatment components (essential oils, additives, therapeutic medications, etc.) are then poured into the fluid chamber 32 through the fill port 33 formed in the bottom side of the reservoir 20. Fill plug 35 is then inserted into the fill port 33 to seal the port 33 to prevent leaks (e.g. by engaging corresponding threads therebetween).

Like the device of the parent application, the instant design has an internal transducer 34 for sonically generating vapor from the liquid stored within the fluid chamber 32. As it is intended herein, other non-heat-producing mist/vapor generating devices are interchangable with the transducer 34. For example, the liquid could be drawn from the reservoir 20 and then pressurized, such as by pumping. The pressurized liquid could then be emitted through one or more orifices so that a cool mist is created. Furthermore, it should be understood that the transducer 34 could generate ultrasonic vibrations to create the mist/vapor, or it could also generate sound waves to vaporize the liquid.

Mist or vapor generated by the transducer 34 travels up the mist conduit 38 to the heating chamber 40. The mist conduit 38 is made up a vertical stack and a horizontal stack. The vertical stack is a component attached to the main housing 12, such that it receives its electrical supply (controlled by the control elements on the top of the main housing 12). The horizontal stack is a component fo the removable fluid reservoir 20. Fluid reaches the transducer 34 from a port (not shown) interconnecting the bottom area of the fluid chamber 32 with the transducer 34.

There is a heater module 42 located within the main housing 12 directly adjacent to the heating chamber 40. As cool (non-heated) mist/vapor is generated by the transducer 34, blower 36 creates airflow that drives the mist/vapor down the mist conduit 38 until it reaches the heating chamber 40. If the heater module 42 is activated, the transient mist/vapor will acquire heat as it passes through the heating chamber 40.

Figure 5:
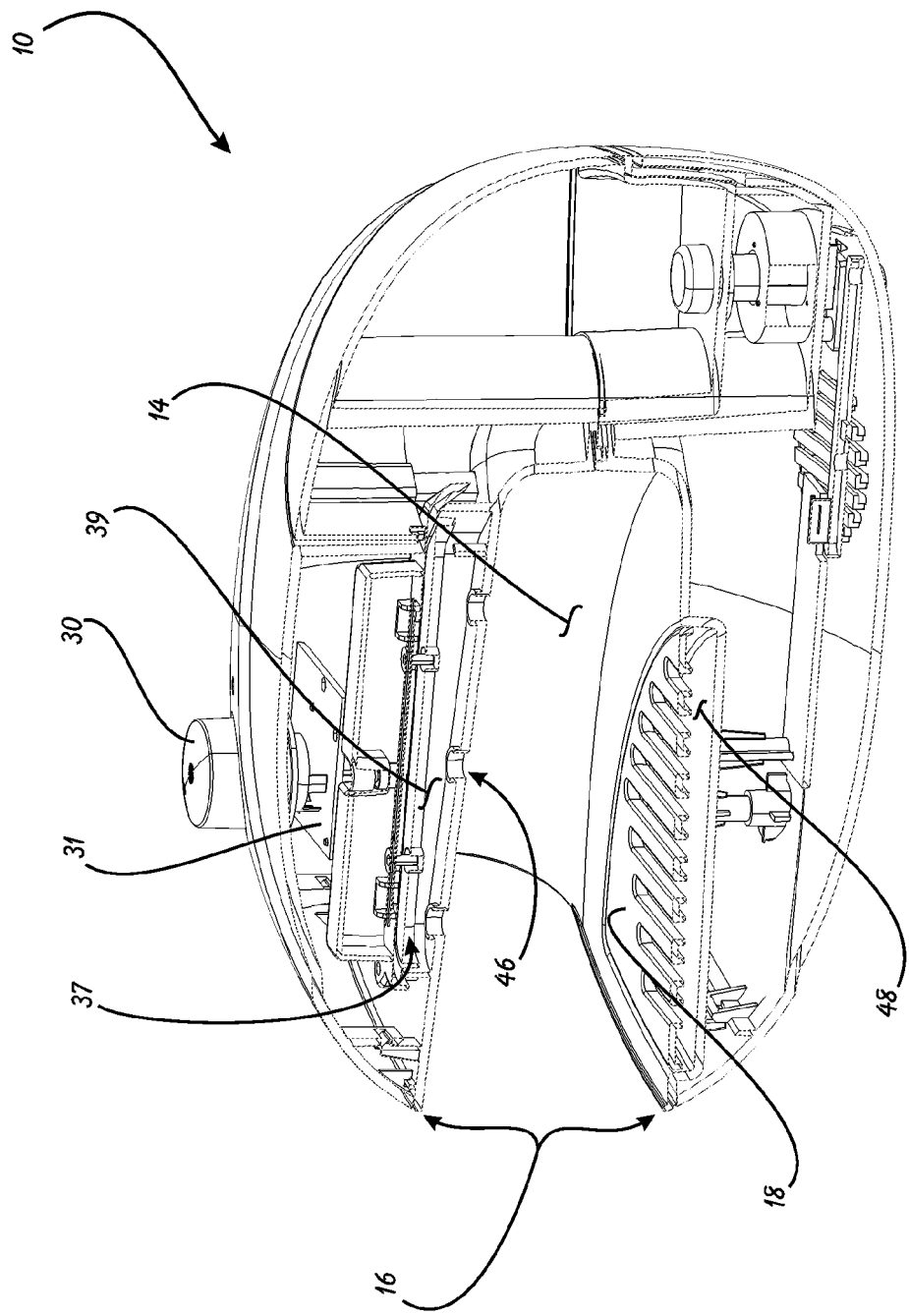
FIG. 5 is a second partially cutaway side view of the device of FIGS. 1-4.

There is a plurality of mist orifices 46 (see FIG. 5) dispersed across the bottom wall of the heating chamber 40. These mist orifices 46 are formed in applicator head 44, and allow fluid to pass between the heating chamber 40 and the treatment chamber 14. As a result, as mist/vapor is driven into the heating chamber 40, it will proceed to flow into the treatment chamber 14 through the mist orifices 46 (see FIG. 5) so that it will flow down onto the user's hands (that are inserted into the treatment chamber 14). FIG. 5 depicts yet another view of the internal components of the device of the current design.

FIG. 5 is a second partially cutaway side view of the device 10 of FIGS. 1-4. In this depiction, we can see that the mist control knob 30 is positioned to operate flow gate 31 to open and close flow opening 37. The gate 31 travels up and down within the flow chamber 39 to throttle the amount of mist/vapor that flows through the flow opening 37 and into the heating chamber 40 (see FIG. 4).

As the mist/vapor condenses within the treatment chamber 14, it can be expected to condense on the user's hands in the form of a liquid once again. In order to prevent the condensed liquid from overflowing and leaking out through the from aperture 16 in the main housing 12, a drain receptacle 48 is formed in the bottom of the treatment chamber 14. The drain receptacle 48 is covered by a drain tray 18 in order to prevent the user from inadvertently dipping his or her hands into the condensed liquid residing in the drain receptacle. If we finally turn to FIG. 6, we can review the entire flow train followed by the air, fluid and mist/vapor as it is transformed and passes through the device in order to provide treatment to the user's hands.

Figure 6:
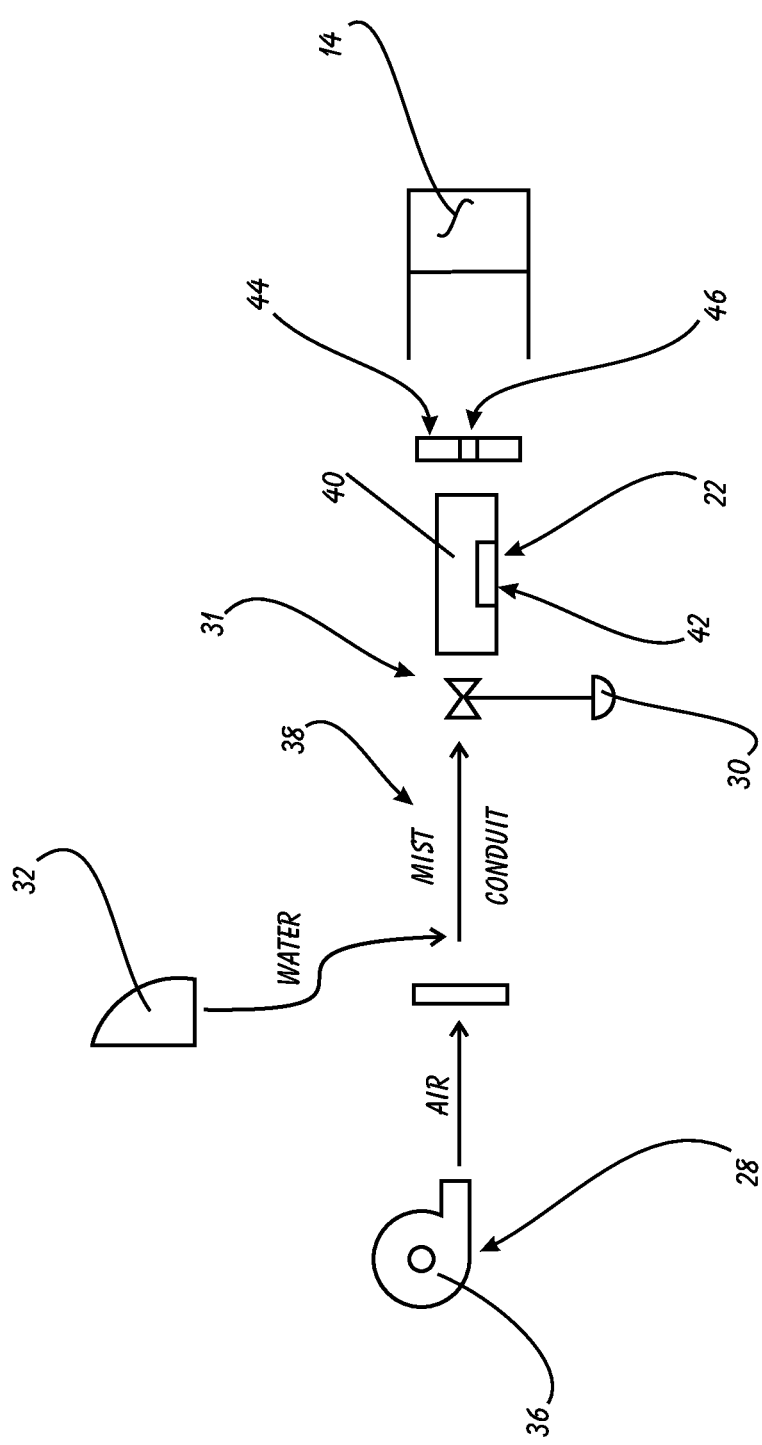
FIG. 6 is a flow diagram depicting the process steps of the method of the present invention.

FIG. 6 is a flow diagram depicting the process steps of the method of the present invention. The blower 36 generates air flow and pressure that is directed to the transducer 34. The blower 36 rotational speed (and therefore the speed of the airflow) is controlled by the air control knob 28. Water (or whatever treatment liquid is contained within the fluid chamber 32) is fed by gravity from the fluid chamber 32 into the transducer 34, where it is vaporized by cool, ultrasonic agitation. Air from the blower 36 mixes with the vapor and drives the mist/vapor down the mist conduit 38. As it reaches the end of the mist conduit 38, the vapor/mist flowrate is controlled by the flow gate 31 (which is controlled by the user through operation of the mist control knob).

As vapor/mist exits past the flow gate 31, it enters the heating chamber 40 and comes in contact with the heater module 42. If, according to the user input to the mode control button, the heater module 42 is activated, the mist/vapor will be heated as it passes through the heating chamber 40. If the heater module 42 is not activated, then only cool vapor/mist will pass through the heating chamber 40.

Ultimately, mist/vapor will be driven through the heating chamber 40 and into the treatment chamber 14 through one or more mist orifices 46 formed in the "roof" of the treatment chamber 14. The result will be a pleasing, therapeutic cascade of vapor blanketing the user's hands in order to improve skin moisture and overall condition.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A vaporizer device, comprising:
a base assembly comprising:
    a liquid reservoir;
    a vaporizer element configured to vaporize liquid fed to said vaporizer from said liquid reservoir, said vaporizer element forming cool vapor by vaporizing said liquid without the prior application of heat to said liquid;
    a treatment chamber internal to said base assembly;
    an applicator head forming a wall of said treatment chamber;
    a mist conduit in fluid communication with said vaporizer element and said applicator head; and
    a heater module located within said applicator head for selectively heating said vaporized liquid in said mist conduit before it exits said applicator head.

2. The device of claim 1, wherein said treatment chamber is contained within a main housing, said treatment chamber being accessible through an aperture formed in said main housing.

3. The device of claim 2, said base assembly further comprising said main housing, said housing further defined by said vaporizer element, said vaporizer element being a sonic transmitter.

4. The device of claim 3, where said main housing is further defined by a reservoir recess formed in a top side of said base element, said sonic transmitter located in said reservoir recess and said liquid reservoir comprising a detachable tank at least partially insertable into said reservoir recess.

5. The device of claim 4, wherein said applicator head is further defined by a face, said face defined by at least one mist orifice in fluid communication with said mist conduit.

6. The device of claim 5, further comprising a heating chamber in fluid communication with said mist conduit and said applicator head, said heater module located in said heating chamber.

7. The device of claim 6, further comprising a flow chamber interconnecting said heating chamber and said applicator head, said flow chamber separated from said applicator head by a flow opening.

8. The device of claim 7, further comprising a flow gate operable to seal and unseal said flow opening.

9. The device of claim 8, further comprising a mist control knob protruding from said main housing, said mist control knob operable to change the position of said flow gate.

10. The device of claim 9, wherein said main housing comprises a top, a bottom and a peripheral side, said treatment chamber aperture formed in said peripheral side.

11. The device of claim 10, wherein said treatment chamber is defined by a top and a bottom, said one or more mist orifices located in said top of said treatment chamber.

12. The device of claim 11, further comprising a drain receptacle formed in said bottom of said treatment chamber, said drain receptacle further comprising a drain tray inserted therein.

13. A device for cleansing and hydrating a human's hands, comprising:
    a main housing;
    a liquid reservoir;
    a vaporizer element configured to vaporize liquid fed to said vaporizer from said liquid reservoir, said vaporizer element forming cool vapor by vaporizing said liquid without the prior application of heat to said liquid;
    a treatment chamber internal to said main housing;
    an applicator head forming a wall of said treatment chamber;
    a mist conduit in fluid communication with said vaporizer element and said applicator head; and
    a heater module located within said applicator head for selectively heating said vaporized liquid in said mist conduit before it exits said applicator head, the operation of said heater module controlled by a mode control button located on an outer surface of said main housing.

14. The device of claim 13, wherein said treatment chamber is contained within a main housing, said treatment chamber being accessible through an aperture formed in said main housing.

15. The device of claim 14, wherein said main housing comprises a top, a bottom and a peripheral side, and said treatment chamber aperture is formed in said peripheral side.

16. The device of claim 15, wherein said treatment chamber is defined by a top and a bottom, and one or more mist orifices located in said top of said treatment chamber.

17. A method for treating the skin of the hands, comprising the steps of:
    placing one or more hands into a treatment chamber formed in a main housing;

generating a mist by applying mechanical vibration to a fluid to vaporize said fluid, said generating conducted within said main housing;

selectively heating said vaporized fluid within a heating chamber; and blowing said vaporized fluid down a mist conduit and out through one or more orifices formed in a wall of said treatment chamber, said heating conducted after said mist generating step.

18. The method of claim 17, further comprising the step of mixing water with one or more other ingredients prior to said mist generating step.

19. The method of claim 18, wherein said other ingredients of said mixing step are selected from the group of extracts, additives, therapeutic medications and essential oils.

* * * * *